United States Patent [19]
Bryan et al.

[11] Patent Number: 5,141,671
[45] Date of Patent: Aug. 25, 1992

[54] MIXED LIGAND 8-QUINOLINOLATO ALUMINUM CHELATE LUMINOPHORS

[75] Inventors: Philip S. Bryan; Frank V. Lovecchio, both of Webster; Steven A. VanSlyke, Rochester, all of N.Y.

[73] Assignee: Eastman Kodak Company, Rochester, N.Y.

[21] Appl. No.: 738,751

[22] Filed: Aug. 1, 1991

[51] Int. Cl.$^5$ .......................... C09K 11/06; C07F 5/06
[52] U.S. Cl. .......................... 252/301.16; 252/301.26; 546/7
[58] Field of Search .......................... 546/7; 313/504; 252/301.16, 301.26

[56] References Cited

U.S. PATENT DOCUMENTS

| | | | |
|---|---|---|---|
| 2,608,556 | 7/1950 | Kalberg | 546/7 |
| 2,864,771 | 12/1958 | Switzer | 252/301.16 |
| 3,163,530 | 12/1964 | Schlesinger | 546/7 |
| 3,567,932 | 3/1971 | Alburger | 546/7 |
| 4,539,507 | 9/1985 | VanSlyke et al. | 313/504 |
| 4,720,432 | 1/1988 | VanSlyke et al. | 428/457 |
| 4,769,292 | 9/1988 | Tang et al. | 428/690 |
| 4,775,820 | 10/1988 | Eguchi | 313/504 |
| 4,885,211 | 12/1989 | Tang et al. | 428/457 |
| 4,950,950 | 8/1990 | Perry et al. | 313/504 |

FOREIGN PATENT DOCUMENTS

| | | |
|---|---|---|
| 0509299 | 1/1955 | Canada . |
| 2-008287 | 1/1990 | Japan . |
| 2-255790 | 10/1990 | Japan . |

*Primary Examiner*—Prince Willis, Jr.
*Assistant Examiner*—Thomas Steinberg
*Attorney, Agent, or Firm*—J. Jeffrey Hawley

[57] ABSTRACT

A blue-emitting luminescent composition is disclosed comprised of an aluminum chelate containing a phenolato ligand and two $R^5$-8-quinolinolato ligands, where $R^5$ substituents are chosen to block the attachment of more than two substituted 8-quinolinolato ligands to the aluminum atom. The presence of the phenolato ligand shifts emission to the blue region of the spectrum. Emission can be shifted to even shorter blue wavelengths by the incorporation of a pentacarbocyclic aromatic fluorescent dye.

30 Claims, 1 Drawing Sheet

FIG. 1

MIXED LIGAND 8-QUINOLINOLATO ALUMINUM CHELATE LUMINOPHORS

FIELD OF THE INVENTION

The invention relates to novel luminescent compositions.

BACKGROUND OF THE INVENTION

Materials that can be stimulated to emit light, commonly referred to as luminescent materials or luminophors, can be employed in a wide variety of applications. In a simple application a luminophor can be employed to absorb ultraviolet radiation and emit visible light. In other applications one of a variety of different stimulating sources of radiation, such as electrons, $\alpha$ or $\beta$ particles, $\gamma$ rays or X rays, can be employed. In still another type of application, referred to as electroluminescence, the recombination of hole-electron pairs can provide the stimulating energy source for luminescence.

For many luminophor applications there is a need for thin ($<1$ $\mu$m) film luminophors. Often the evironment for deposition is incompatible with coating from solution. Thus, for many applications the luminophors must be capable of being deposited as thin films from a vapor phase. Vapor phase deposition offers the advantages of well controlled film thicknesses, both in terms of uniformity and the rate at which they are formed. Since only the luminophor is required for vapor phase deposition, very high purity films can be formed. Specific examples of luminophors used to construct thin films in an environment requiring vapor deposition are provided by VanSlyke et al U.S. Pat. No. 4,539,507, Tang et al U.S. Pat. No. 4,769,292, VanSlyke et al U.S. Pat. No. 4,720,432, Tang et al U.S. Pat. No. 4,885,211 and Perry et al U.S. Pat. No. 4,950,950.

Through a series of investigations conducted over a period of years preferred green-emitting luminoph,ors capable of vapor deposition and exhibiting high levels of luminescence efficiencies and stabilities have been found to be aluminum trisoxines, a.k.a. tris(-quinolinolato)aluminum(III) chelates. Unfortunately, these chelates are green-emitting luminophors and do not satisfy the need in the art for blue-emitting luminophors having comparable qualities.

RELATED PATENT APPLICATIONS

(RPA-1) VanSlyke U.S. Ser. No. 07/738,776, concurrently filed and commonly assigned, IMPROVED BLUE EMITTING INTERNAL JUNCTION ORGANIC ELECTROLUMINESCENT DEVICE (I) discloses an internal junction organic EL device comprised of, in sequence, an anode, an organic hole injecting and transporting zone, an organic electron injecting and transporting zone, and a cathode. The organic electron injecting and transporting zone is comprised of an electron injecting layer in contact with the cathode and, interposed between the electron injecting layer and the organic hole injecting and transporting zone, a blue emitting luminescent layer comprised of a bis($R^s$-8-quinolinolato)aluminum(III)-$\mu$-oxo-bis($R^s$-8-quinolinolato)aluminum(III) charge accepting compound. $R^s$ is chosen to block the attachment of more than two substituted 8-quinolinolato ring nuclei to any one aluminum atom. Device emission at even shorter wavelengths and increased operating stability can be realized by the incorporation of a pentacarbocyclic aromatic fluorescent dye.

(RPA-2) VanSlyke et al U.S. Ser. No. 07/738,777, concurrently filed and commonly assigned, IMPROVED BLUE EMITTING INTERNAL JUNCTION ORGANIC ELECTROLUMINESCENT DEVICE (II) discloses an internal junction organic EL device comprised of, in sequence, an anode, an organic hole injecting and transporting zone, an organic electron injecting and transporting zone, and a cathode. The organic electron injecting and transporting zone is comprised of an electron injecting layer in contact with the cathode and, interposed between the electron injecting layer and the organic hole injecting and transporting zone, a blue emitting luminescent layer comprised of an aluminum chelate containing a phenolato ligand and two $R^S$-8-quinolinolato ligands, where Rs substituents are chosen to block the attachment of more than two substituted 8-quinolinolato ring nuclei to the aluminum atom. The presence of the phenolato ligand shifts device emission to the blue region of the spectrum and increases emission efficiency. Device emission at even shorter blue wavelengths and increased operating stability can be realized by the incorporation of a pentacarbocyclic aromatic fluorescent dye.

SUMMARY OF THE INVENTION

It is an object of this invention to provide a novel luminescent composition that is blue-emitting, and capable of vapor deposition.

In one aspect the invention is directed to a blue emitting luminescent composition comprised of an aluminum chelate of the formula:

$$(R^S-Q)_2-Al-O-L$$

where

Q in each occurrence represents a substituted 8-quinolinolato ligand, $R^S$ represents an 8-quinolinolato ring substituent chosen to block sterically the attachment of more than two substituted 8-quinolinolato ligands to the aluminum atom, O-L is phenolato ligand, and L is a hydrocarbon of from 6 to 24 carbon atoms comprised of a phenyl moiety.

In another aspect, the invention is directed to a composition of the type described further characterized in that the composition additionally includes a fluorescent dye.

DESCRIPTION OF PREFERRED EMBODIMENTS

The present invention is directed to a novel luminescent composition that is blue emitting, and capable of vapor deposition. The composition is suited in terms of luminescence, vapor deposition characteristics, stability and electroluminescence efficiency for incorporation in an organic EL device as the luminescent layer.

The terms "blue emitting" and "green emitting" are easy enough to understand and identify in most instances; but since there is a continuous spectrum of hues ranging from pure blue to pure green, a quantitative basis is required for precise delineation. This quantita- tive basis is provided by the 1931 C.I.E. chromaticity diagram shown in FIG. 1. The 1931 C.I.E. chromaticity diagram is a widely accepted approach for quantifying hue within the visible spectrum. A full explanation of the 1931 C.I.E. chromaticity diagram is provided by Wyszecki and Stiles, Color Science, Concepts and Methods: Quantitative Data and Formulae, 2nd Ed., Chapter 3, Colorimetry, Wiley, 1982, pp. 117-143, and more succinct explanation is provided by James, The Theory of the Photographic Process, 4th Ed., Macmillan, 1977, Chapter 19, II, B. Colorimetry, pp 563-565.

Figure 1:
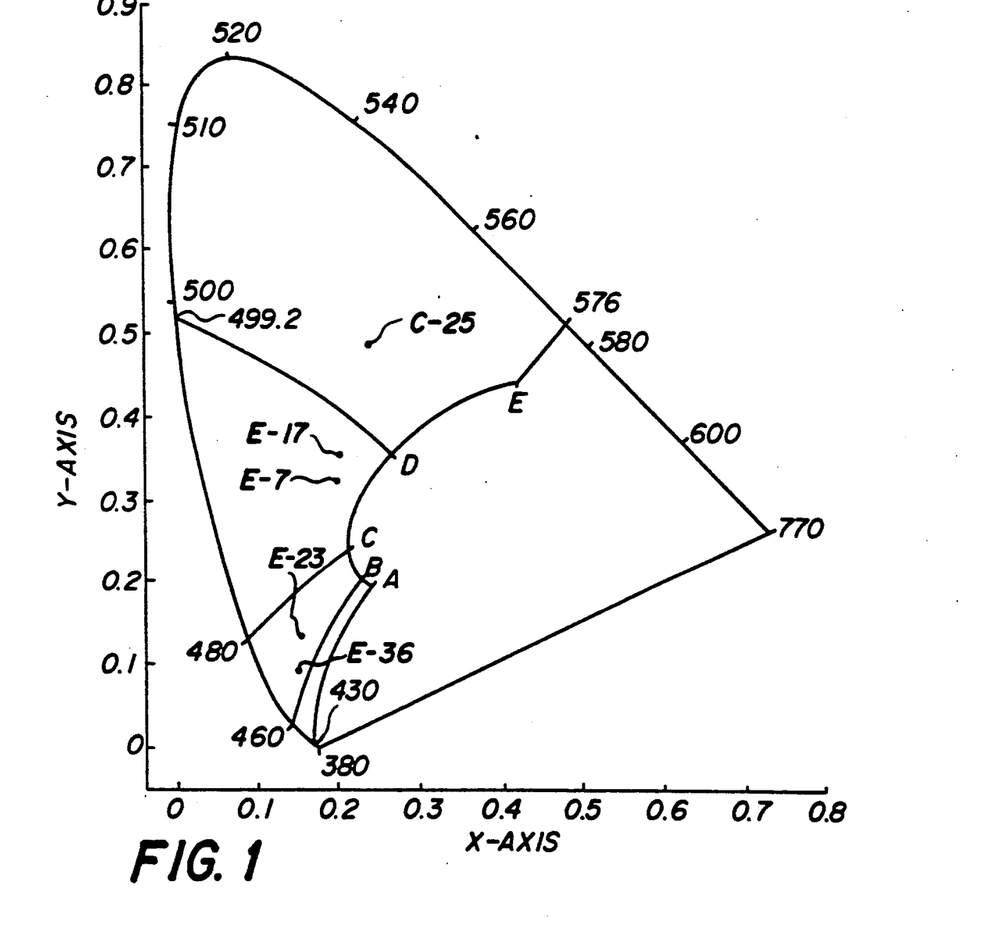
FIG. 1 is a 1931 C.I.E. chromaticity diagram with color regions of specific interest delineated.

Referring to FIG. 1, fully saturated monochromatic hues ranging from 380 to 770 nm form a curve defining the saturation boundaries of the visible spectrum. Hues that lie within the curve boundary are to some extent desaturated, meaning that they tend more toward white. The x and y axes are employed as descriptors for precisely locating each visible hue.

As herein employed the term "blue emitting" refers to the area of the diagram defined by the points extending from 430 to 499.2 nm to D, C, B and A and back to 430 nm. The area extending from 460 to 480 nm to C to B and back to 460 nm is perceived by the eye as being blue. The area extending from 430 to 460 nm to B to A and back to 430 nm is perceived by the eye as being bluish purple. The area extending from 480 to 499.2 nm to D to C and back to 480 nm is perceived by the eye as being greenish blue or bluish green. The area to right of points A, B, C and D are excluded, since the hue is so desaturated that the visual perception is primarily that of white.

As herein employed the term "green emitting" refers to the area of the diagram defined by the points extending from 499.2 to 576 nm to E and D and back to 499.2 nm. It is in this area of the spectrum that conventional green emitting organic EL devices emit. To the right of the boundary defined by 499.2 and D the observed hue is green while the left of the boundary defined by 576 and E the observed hue is greenish yellow.

The blue emitting luminescent composition is comprised of a mixed ligand aluminum chelate, apecifically a bis($R^S$-8-quinolinolato)(phenolato)aluminum(III) chelate, where $R^S$ is a ring substituent of the 8-quinolinolato ring nucleus chosen to block the attachment of more than two 8-quinolinolato ligands to the aluminum atom. These compounds can be represented by the formula:

$(R^S-Q)_2-Al-O-L$ where

Q in each occurrence represents a substituted 8-quinolinolato ligand, $R^S$ represents an 8-quinolinolato ring substituent chosen to block sterically the attachment of more than two substituted 8-quinolinolato ligands to the aluminum atom, O-L is phenolato ligand, and L is a hydrocarbon of from 6 to 24 carbon atoms comprised of a phenyl moiety.

The advantage of employing an aluminum chelate with two substituted 8-quinolinolato ligands and a phenolato ligand is that all of the desirable physical properties of tris(8-quinolinolato)aluminum(III) chelates, the preferred green emitting luminophors of organic EL devices, are retained while emission is shifted to the blue region of the spectrum. More specifically, the combination of two substituted 8-quinolinolato ligands and a phenolato ligand produces an aluminum chelate that can be deposited from the vapor phase to form the electron transporting layer of the organic EL device. Vapor phase deposition is the preferred approach to construction of the organic layer sequence of organic EL devices. Vapor phase deposition allows extremely thin layers of well controlled thickness and uniformity to be deposited. No solvents or other extraneous materials need be brought into contact with the deposition substrate, the hole injecting and transporting zone, that would dissolve, contaminate or degrade the performance of this substrate zone. Vapor phase deposition has the further advantage of allowing the rate of deposition to be controlled and of allowing greater freedom and flexibility in device construction.

The presence of the phenolato ligand is responsible for shifting emissions to the blue portion of the spectrum. As employed herein the term "phenolato ligand" is employed in its art recognized usage to mean a ligand bonded to the aluminum atom by the deprotonated hydroxyl group of a phenol.

In its simplest form the phenolato ligand can be provided by deprononation of hydroxybenzene. Ultraviolet stimulation has demonstrated that peak emission at a shorter wavelength than 500 nm can be realized. Testing in organic EL devices has established acceptable stability (retention of at least a half of initial luminescent intensity for more than 50 hours).

In an effort to improve performance, substituted phenols were investigated. It was observed that methoxy and dimethoxy substituted phenolato ligands exhibited relatively weak luminescent intensities. Since methoxy substituents are electron donating, phenols were also investigated with strongly electron withdrawing substituents, such as halo, cyano and α-haloalkyl substituents. Aluminum chelates with these ligands, though luminophors, did not undergo successful vapor phase conversions.

From further investigations, illustrated by the Examples below, it has been determined that the preferred phenolato ligands for the aluminum chelates of formula I are derived from HO-L phenols, where L is a hydrocarbon of from 6 to 24 carbon atoms comprised of a phenyl moiety This includes not only hydroxybenzene, but a variety of hydrocarbon substituted, hydroxybenzenes, hydroxynaphthalenes and other fused ring hydrocarbons. Since monomethyl substitution of the phenyl moiety shortened emission wavelengths, it is preferred that the phenolato ligand contain at least 7 carbon atoms. Generally there is little advantage to be gained by employing phenolato ligands with very large numbers of carbon atoms. However, investigations of phenolato ligands with 18 aromatic ring carbon atoms have revealed high levels of stability. Thus, the phenoloato ligands preferably contain from 7 to 18 total carbon atoms.

Aliphatic substituents of the phenyl moiety of phenolato ligand are contemplated to contain from 1 to 12 carbon atoms each. Alkyl phenyl moiety substituents of from 1 to 3 carbon atoms are specifically preferred, with the best overall characteristics having been observed to be produced with methyl substituents.

Aromatic hydrocarbon substituents of the phenyl moiety are preferably phenyl or naphthyl rings. Phenyl, diphenyl and triphenyl substitution of the phenyl moiety have all been observed to produce highly desirable organic EL device characteristics.

Phenolato ligands derived from α or β naphthols have been observed to produce aluminum chelates of exceptional levels of stability. A limited degree of emission shifting to shorter wavelengths is also realized, similar to that exhibited by hydroxybenzene derived phenolato ligands. By employing naphtholato ligand containing aluminum chelates in combination with blue emitting fluorescent dyes, described below, highly desirable device constructions are possible.

From comparisons of ortho, meta and para substituted homologues of the various phenolato ligands it has b,een determined that little, if any, difference in performance is attributable to the position on the phenyl moiety ring occupied by the hydrocarbon substituent.

In a preferred form the aluminum chelates satisfy the following formula:

where
Q and $R^S$ are as defined above and
$L^1$, $L^2$, $L^3$, $L^4$ and $L^5$ collectively contain 12 or fewer carbon atoms and each independently represent hydrogen or hydrocarbon groups of from 1 to 12 carbon atoms, with the proviso that $L^1$ and $L^2$ together or $L^2$ and $L^3$ together can form a fused benzo ring.

Although either or both of the 8-quinolinolato rings can contain substituents other than the steric blocking substituent, further substitution of the rings is not required. It is appreciated further that more than one substituent per ring can contribute to steric blocking. The various steric blocking substituent possibilities are most easily visualized by reference to the following formula:

where L can take any form described above and $R^2$ to $R^7$ represent substitutional possibilities at each of ring positions 2 to 7 inclusive of the 8-quinolinolato rings. Substituents at the 4, 5 and 6 ring positions are not favorably located to hinder sterically the bonding of three 8-quinolinolato nuclei to a single aluminum atom. While it is contemplated that large substituents at the 3 or 7 ring positions could provide sufficient steric hindrance, the incorporation of bulky substituents substantially increases molecular weight without enhancing molecular performance and therefore detracts from overall performance. On the other hand, the 2 ring position is suited to provide steric hindrance, and even a very small substituent (e.g., a methyl group) in one of these ring positions provides an effective steric blocking substituent. For synthetic convenience it is specifically preferred that steric blocking substituents be located in the 2 ring positions. As employed herein the term "steric blocking is employed to indicate that the $R^S$-Q ligand is incapable of competing for inclusion as the third ligand of the aluminum atom.

Although the phenolato ligand is primarily relied upon to obtain blue emission, it has been observed that substituents to the 8-quinolinolato rings can also perform useful hue shifting functions. The quinoline ring consists of fused benzo and pyrido rings. When the pyrido ring component of the quinoline ring is substituted with one or more electron donating substituents the effect is to shift the hue of emission to shorter wavelengths. That is, emission is shifted away from the green region of the spectrum and toward a more primary blue emission. Electron donating substituents at the ortho and para positions of the pyrido ring (that is, the 2 and 4 positions of the quinoline ring) particularly influence the hue of emission, while the meta position on the pyrido ring (the 3 position on the quinoline ring) has a comparatively small influence on the hue of emission. It is, in fact, recognized that an electron accepting substituent could, if desired, be located at the 3 ring position while retaining a blue emission characteristic. Although steric hindrance is entirely independent of electron donating or accepting properties and, thus, $R^2$ can in theory take the form of either an electron donating or accepting group, it is preferred to choose $R^2$ from among electron donating groups. By adding a second electron donating group R4 a further shift in hue away from the green portion of the spectrum is achieved. $R^3$, when present, can take any synthetically convenient form, but is preferably also electron donating.

By contrast electron accepting substituents of the benzo ring component of the quinoline nucleus shift the hue of emission toward shorter wavelengths. Thus, any or all of substituents at the 5, 6 and 7 quinoline ring positions, when present, are preferably electron accepting.

It is well within the skill of the art to determine whether a particular substituent is electron donating or electron accepting. The electron donating or accepting properties of several hundred of the most common substituents, reflecting all common classes of substituents have been determined, quantified and published. The most common quantification of electron donating and accepting properties is in terms of Hammett $\sigma$ values. Substituents with negative Hammett $\sigma$ values are electron donating while those with positive Hammett $\sigma$ values are electron accepting. Hydrogen has a Hammett $\sigma$ value of zero, while other substituents have Hammett $\sigma$ values that increase positively or negatively in direct relation to their electron accepting or donating characteristics. Lange's Handbook of Chemistry, 12th Ed., McGraw Hill, 1979, Table 3-12, pp. 3-134 to 3-138, here incorporated by reference, lists Hammett $\sigma$ values for a large number of commonly encountered substituents. Hammett $\sigma$ values are assigned based on phenyl ring substitution, but they provide a workable guide for qualitatively selecting electron donating and accepting substituents for the quinoline ring.

Taking all factors together, steric blocking, synthetic convenience, and electron donating or accepting properties, $R^2$ is preferably an amino, oxy or hydrocarbon substituent. Adequate steric hindrance is provided when $R^2$ is methyl and is the sole 8-quinolinolato ring substituent (i.e., each of $R^3$, $R^4$, $R^5$, $R^6$ and $R^7$ is hydrogen). Thus, any amino, oxy or hydrocarbon substituent having at least 1 carbon atom falls within the perview of preferred substituents. Preferably no more than 10 carbon atoms are present in any one hydrocarbon moiety and optimally no more than 6 carbon atoms. Thus, $R^2$ preferably takes the form of —R', —OR' or —N(R")R', where R' is a hydrocarbon of from 1 to 10 35 carbon atoms and R" is R' or hydrogen. Preferably $R^2$ contains 10 or fewer carbon atoms and optimally 6 or fewer carbon atoms.

$R^3$ and $R^4$ for the reasons set forth above can take a broader range of forms than $R^2$, but are specifically contemplated to be selected from among the same group of preferred substituents as $R^2$. Since 3 and 4 ring position substitution is not required, $R^3$ and $R^4$ can additionally be hydrogen.

Since 5, 6 or 7 ring position substitution is not required, $R^5$, $R^6$ and $R^7$ can represent hydrogen. In preferred forms $R^5$, $R^6$ and $R^7$ can be selected from synthetically convenient electron accepting substituents, such as cyano, halogen, and α-haloalkyl, α-haloalkoxy, amido, sulfonyl, carbonyl, carbonyloxy and oxycarbonyl substituents containing up to 10 carbon atoms, most preferably 6 or fewer carbon atoms.

The following constitute specific examples of preferred mixed ligand aluminum chelates satisfying the requirements of the invention:

PC-1

Bis(2-methyl-8-quinolinolato)(phenolato)aluminum(III)

PC-2

Bis(2-methyl-8-quinolinolato)(ortho-cresolato)aluminum(III)

PC-3

Bis(2-methyl-8-quinolinolato)(meta-cresolato)aluminum(III)

PC-4

Bis(2-methyl-8-quinolinolato)(para-cresolato)aluminum(III)

PC-5

Bis(2-methyl-8-quinolinolato)(ortho-phenylphenolato)aluminum(III)

PC-6

Bis(2-methyl-8-quinolinolato)(meta-phenylphenolato)aluminum(III)

PC-7
Bis(2-methyl-8-quinolinolato)(para-phenyl-phenolato)aluminum(III)

PC-8
Bis(2-methyl-8-quinolinolato)(2,3-dimethyl-phenolato)aluminum(III)

PC-9
Bis(2-methyl-8-quinolinolato)(2,6-dimethyl-phenolato)aluminum(III)

PC-10
Bis(2-methyl-8-quinolinolato)(3,4-dimethyl-phenolato)aluminum(III)

PC-11
Bis(2-methyl-8-quinolinolato)(3,5-dimethyl-phenolato)aluminum(III)

PC-12
Bis(2-methyl-8-quinolinolato)(2,3-di-tert-butyl-phenolato)aluminum(III)

PC-13
Bis(2-methyl-8-quinolinolato)(2,6-dimethyl-phenolato)aluminum(III)

PC-14
Bis(2-methyl-8-quinolinolato)(2,4,6-triphenyl-phenolato)aluminum(III)

PC-15
Bis(2-methyl-8-quinolinolato)(2,3,6-trimethyl-phenolato)aluminum(III)

PC-16
Bis(2-methyl-8-quinolinolato)(2,3,5,6-tetramethyl-phenolato)aluminum(III)

PC-17
Bis(2-methyl-8-quinolinolato)(1-naphtholato)aluminum(III)

PC-18
Bis(2-methyl-8-quinolinolato)(2,4,6-2-naphtholato)aluminum(III)

PC-19
Bis(2,4-methyl-8-quinolinolato)(2,4,6-orthophenyl-phenolato)aluminum(III)

PC-20
Bis(2,4-dimethyl-8-quinolinolato)(paraphenyl-phenolato)aluminum(III)

PC-21
Bis(2,4-dimethyl-8-quinolinolato)(metaphenyl-phenolato)aluminum(III)

PC-21
Bis(2,4-dimethyl-8-quinolinolato)(3,5-dimethyl-phenolato)aluminum(III)

PC-23
Bis(2,4-dimethyl-8-quinolinolato)(3,5-ditert-butyl-phenolato)aluminum(III)

Although the luminescent blue-emitting composition can consist of any one or combination of the mixed ligand aluminum(III) chelates described above, it is specifically contemplated to employ in combination with the mixed ligand alumuminum(III) chelates one or a combination of fluorescent dyes following the teachings of Tang et al U.S. Pat. No. 4,769,292, cited above, the disclosure of which is here incorporated by reference. Any blue emitting combination of one or more fluorescent dyes and one or more compounds satisfying formula I can be employed. Three distinctly different categories of combinations are possible that permit blue emission:

In a first category, a blue-emitting luminescent composition can be formed by blending a compound satisfying formula I, which in this instance serves as a host compound, with a blue emitting fluorescent dye chosen to provide a favored recombination site for holes and electrons received from the charge accepting compound. In this arrangement the host and fluorescent dye relationship taught by Tang et al is present. When this relationship is favored the fluorescent dye exhibits a reduction potential less negative than that of the host compound, the fluorescent dye exhibits a lower bandgap potential than that of the host compound, and the host compound and fluorecent dye are spectrally coupled—that is, the host compound has a capability when used alone to,emit at a wavelength that corresponds to an absorption wavelength of the fluorescent dye. For optimum coupling it is preferred that the peak emission wavelength of the host correspond to the peak absorption wavelength of the fluorescent dye within ±100 nm, optimally ±25 nm. Blue emitting fluorescent dyes are required in this instance, since the hue of emission is entirely determined by the fluorescent dye.

In a second category the relationships and roles of the formula I compound and the fluorescent dye are simply reversed. The fluorescent dye acts as the host compound while the formula I compound is responsible for blue emission. For this relationship to be favored the formula I compound exhibits a reduction potential less negative than that of the host compound, the formula I compound exhibits a lower bandgap potential than that of host compound, and the host compound and formula I compound are spectrally coupled—that is, the host compound has a capability when used alone to emit at a wavelength that corresponds to an absorption wavelength of the formula I compound. For optimum coupling it is preferred that the peak emission wavelength of the host correspond to the peak absorption wavelength of the formula I compound within ±100 nm, optimally ±25 nm.

When neither of the first and second category conditions are sufficiently satisfied to allow emission solely from the fluorescent dye or the formula I compound, as contemplated by the first and second categories above, respectively, a third category is present in which each of the fluorescent dye and the formula I compounds emits at the same wavelength it emits in the absence of the other. In this instance it is preferred that both the formula I compound and the fluorescent dye be blue emitting.

By choosing a fluorescent dye having a peak emission at a shorter wavelength than that of formula I compound a shift to shorter wavelength organic EL device emissions can be realized in either of the first or third categories of constructions.

It has been discovered quite unexpectedly that by employing a fluorescent dye having a chromophoric unit containing at least 5 fused carbocyclic aromatic rings (hereinafter referred to as a pentacarbocyclic aromatic fluorescent dye) increased stability of organic EL device operation is achieved and a shift to shorter wavelengths of blue emission can be realized.

The pentacarbocyclic aromatic fluorescent dyes have been discovered to be highly advantageous for reducing the wavelength of organic EL device emission. To function in a first category arrangement it is essential that the fluorescent dye absorb at a wavelength corresponding to an emission wavelength of the host compound, in this instance the formula I compound. On the other hand, it is recognized that all fluorescent dyes emit at a longer wavelength than they absorb. Stated another way, a dye cannot emit light of a higher energy level than its absorbs. The difference between the longest wavelength absorption maxima (hereinafter referred to as the peak absorption) and the shortest wavelength emission maxima (hereinafter referred to as the peak emission) of a fluorescent dye is known as its Stokes shift. If the Stokes shift of a fluorescent dye is large, it is difficult to achieve efficient spectral coupling and still achieve peak emission at a shorter wavelength than that of the formula I compound. Pentacarbocyclic aromatic fluorescent dyes are particularly suited for shifting organic EL device emissions to shorter blue wavelengths, since they exhibit Stokes shifts of from 80 nm to less than 20 nm, attributable to their relatively rigid chromophoric units. Thus, a hypsochromic shift in organic EL device emission can be realized even though the absorption peak of the pentacarbocyclic aromatic fluorescent dye is only 20 nm shorter in wavelength than the emission peak of the formula I compound. Preferred pentacarbocyclic aromatic fluorescent dyes are those that exhibit an absorption peak at wavelengths ranging from 100 to 20 nm shorter than the emission peak exhibited by the formula I compound.

The pentacarbocyclic aromatic fluorescent dyes contemplated each contain at least 5 fused carbocyclic aromatic rings, which form a chromophoric unit. Fused aromatic carbocyclic rings in addition to the 5 required fused rings do not detract from performance characteristics. Preferred chromophoric units contain a perylene, benzopyrene, benzochrysene, benzonaphthacene, picene, pentaphene, pentacene, hexacene or anthanthrene nucleus, as the entire nucleus or fused with other aromatic rings to complete the nucleus. Typically these dyes contain from 20 to 40 ring carbon atoms. The following is a listing of fused carbocyclic ring compounds that can form the entire dye or a chromophoric unit of a dye contemplated for use in the practice of the invention:

Perylene   FD-1

Benzo[b]perylene   FD-2

Dibenzo[b,pqr]perylene   FD-3

Tribenzo[fg,hi,st]pentacene   FD-4

Dibenzo[fg,qr]pentacene   FD-5

Dibenzo[fg,ij]pentaphene   FD-6

-continued

Benzo[pqr]perylene   FD-7

Dibenzo[ij,rst]pentaphene   FD-8

Tribenzo[b,ghi,n]perylene   FD-9

Tribenzo[cd,fg,l]pyrene   FD-10

Tetrabenzo[a,b,cd,pq]naphthacene   FD-11

-continued

Pentabenzo[b,e,h,jk,mn]pyrene     FD-12

Tetrabenz[a,cd,fg,n]anthanthrene     FD-13

Tetrabenz[b,hi,k,qr]anthanthrene     FD-14

Benzo[a]pyrene     FD-15

Dibenzo[b,d]pyrene     FD-16

Dibenzo[a,e]pyrene     FD-17

Dibenzo[b,h]pyrene     FD-18

Tribenzo[a,e,i]pyrene     FD-19

Tribenzo[b,e,h]pyrene     FD-20

Dibenzo[e,l]pyrene     FD-21

Dibenzo[a,h]pyrene     FD-22

Dibenzo[b,mn]chrysene     FD-23

Dibenzo[de,qr]naphthacene     FD-24

Dibenzo[c,mn]chrysene     FD-25

Tetrabenzo[hi,j,k,qr]anthanthrene     FD-26

Tribenzo[a,c,de]naphthacene     FD-27

Dibenzo[fg,st]pentacene     FD-28

Dibenzo[hi,pq]anthanthrene     FD-29

Dibenzo[opq,stu]picene     FD-30

Hexacene     FD-31

These pentacarbocyclic aromatic rings have the advantage that they can be deposited by vacuum vapor deposition, similarly as the other components of the organic medium. Since the pentacarbocyclic aromatic rings represent chromophores in and of themselves, it is not necessary that other ring substituents be present. However, many dyes containing pentacarbocyclic aromatic rings as chromophores are conventional, having been originally prepared for use in solution chemistry and therefore having substituents intended to modify solubility and, in some instances, hue. Various ring substituents of the pentacarbocyclic aromatic rings of the types disclosed by Tang et al, cited above, are contemplated.

When fluorescent pentacarbocyclic aromatic dyes are incorporated in a formula I host compound in a first category combination, only a small amount of the fluorescent dye is required to realize advantages. Fluorescent pentacarbocyclic aromatic dyes are preferably incorporated in a concentration ranging from 0.05 to 5 mole percent, based on the moles of formula I compound. A specifically preferred concentration range is from 0.2 to 3 mole percent, based on the moles of formula I compound, with a concentration range of from 0.5 to 2 mole percent, based on the moles of charge accepting compound, being in most instances optimum.

EXAMPLES

The invention and its advantages can be better appreciated by the following specific examples.

COMPOUND PREPARATIONS

The following is a description of the preparation and characterization of compounds PC-1 to P-23.

PC-1

A sample of 2-methyl-8-quinolinol (Eastman Kodak Company) was recrystallized from ethanol/water. Then 0.8 g (0.005 mole) of the recrystallized ligand was heated and stirred in 40 mL of absolute ethanol with 1.0 g (0.005 mole) of 99.995% aluminum isopropoxide (Aldrich Chemical Company). After about 30 minutes the solution was filtered through a celite mat to remove a small amount of insoluble material. Then an ethanol solution containing 0.8 g (0.005 mole) of recrystallized 2-methyl-8-quinolinol and 1.0 g (0.01 mole) of phenol (Eastman Kodak Company) was added to the original solution. The resulting solution was heated and stirred at reflux for 4 hours and allowed to cool to room temperature. The solid was collected and washed with ethanol, then ether and allowed to air dry. The solid weighed 1.0 g, which represented a 46% yield.

PC-2 to PC-18

The procedure described above for the preparation of PC-1 was used to prepare the title compounds, except that phenol was replaced with the appropriate substituted phenol. The substituted phenols used to prepare PC-2, PC-4, PC-7, PC-12, PC-13, P-14 and PC-15 were obtained from Aldrich with the remainder of the substituted phenols being obtained from the Eastman Kodak Company. The results are summarized in Table I.

TABLE I

| Compound | Yield % |
|---|---|
| PC-2 | 59 |
| PC-3 | 77 |
| PC-4 | 84 |
| PC-5 | 82 |
| PC-6 | 84 |
| PC-7 | 89 |
| PC-8 | 64 |
| PC-9 | 82 |
| PC-10 | 76 |
| PC-11 | 60 |
| PC-12 | 56 |
| PC-13 | 87 |
| PC-14 | 71 |
| PC-15 | 83 |
| PC-16 | 91 |
| PC-17 | 91 |
| PC-18 | 76 |

PC-19

This alumina chelate was prepared similarly as PC-1, except that 2,4-dimethyl-8-quinolinol was substituted for 2-methyl-8-quinolinol. The orthophenylphenol used was from the Eastman Kodak Company. The title compound yield was 73%.

PC-20

This aluminum chelate was prepared similarly as PC-1, except that 2,4-dimethyl-8-quinolinol was substituted for 2-methyl-8-quinolinol. The paraphenylphenol used was from the Eastman Kodak Company. The title compound yield was 94%.

PC-21

A 1.74 g (0.010 mole) sample of 2,4-dimethyl-8-quinolinol was stirred in 65 mL of anhydrous ether with 1.0 g (0.005 mole) of 99.995% aluminum isoproxide (Aldrich Chemical Company) and 1.7 g (0.010 mole) of meta-phenylphenol (Eastman Kodak Company). The impure solid was collected after 3 hours (0.94 g).

PC-22

A 1.74 g (0.010 mole) sample of 2,4-dimethyl-8-quinolinol was stirred in 75 mL of anhydrous ether with 1.0 g (0.005 mole) of 99.995% aluminum isoproxide (Aldrich Chemical Company) and 1.2 g (0.010 mole) of 3,5-dimethylphenol (Aldrich Chemical Company). The impure solid was collected after 6 hours (2.3 g).

PC-23

A 0.87 g (0.005 mole) sample of 2,4-dimethyl-8-quinolinol was stirred in 40 mL of anhydrous ether with 0.5 g (0.0025 mole) of 99.995% aluminum isoproxide (Aldrich Chemical Company) and 1.0 g (0.005 mole) of 3,5-di-t-butylphenol (Aldrich Chemical Company). The impure solid was collected after 5 hours (0.83 g).

COMPOUND CHARACTERIZATIONS

The compounds prepared were analyzed and compared to theoretical compositions as shown in Table II. This provided confirmation that the intended compounds had been synthesized.

The next task was to determine that the compounds were capable of undergoing vacuum evaporation followed by deposition while retaining their intended structure. For compounds that are capable of undergoing vacuum evaporation without decomposition this procedure has the desirable effect of purifying the materials. In this technique a powder sample was placed in a porcelain boat which was then inserted into a 2.54 cm diameter Pyrex TM tube. Argon was flowed through the tube at a pressure of about 2 torr while the center of the tube was heated in a tube furance. Each of the samples was treated in this way. The solids condensed from the vapor phase were analyzed, and the results are reported in Table II.

The compounds were further evaluated to determine that each was fluorescent. The fluorescence spectrum was recorded for each of the powders as initially prepared. The ultraviolet excited emission spectrum of each powder sample was obtained by packing the powder into a 2.48 cm diameter by 0.24 cm deep aluminum planchet and placing the loaded planchet into a sample chamber of a spectrofluorometer. Each sample was exposed to ultraviolet light with a 4 nm bandwidth centered at 355 nm from a xenon arc lamp that had passed through a monochromator and bandpass filter. The emitted light was collected, passed through an order-sorting filter and detected by a spectrometer which was calibrated to within ±1 nm with a resolution of approximately 4 nm (full width at half maximum).

The wavelength of maximum intensity emission is provided in Table II.

TABLE II

| Compound | $\lambda_{max}$ | Theoretical % N | Theoretical % C | Theoretical % H | Initial Powder (Observed) % N | Initial Powder (Observed) % C | Initial Powder (Observed) % H | Sublimed Powder (Observed) % N | Sublimed Powder (Observed) % C | Sublimed Powder (Observed) % H |
|---|---|---|---|---|---|---|---|---|---|---|
| 1 | 473 | 6.42 | 71.55 | 4.85 | 6.49 | 71.05 | 4.95 | 6.49 | 71.22 | 4.91 |
| 2 | 466 | 6.22 | 71.99 | 5.15 | 6.34 | 71.21 | 5.12 | 6.23 | 71.89 | 5.18 |
| 3 | 477 | 6.22 | 71.99 | 5.15 | 5.74 | 68.54 | 5.29 | 6.16 | 71.98 | 5.20 |
| 4 | 473 | 6.22 | 71.99 | 5.15 | 6.08 | 71.20 | 5.13 | 6.07 | 71.53 | 5.06 |
| 5 | 466 | 5.47 | 74.99 | 4.92 | 5.42 | 74.84 | 5.03 | 5.43 | 74.99 | 5.01 |
| 6 | 454 | 5.47 | 74.99 | 4.92 | 5.35 | 74.50 | 5.02 | 5.42 | 74.80 | 5.00 |
| 7 | 473 | 5.47 | 74.99 | 4.92 | 5.37 | 74.04 | 4.97 | 5.43 | 74.51 | 4.96 |
| 8 | 471 | 6.03 | 72.40 | 5.43 | 6.06 | 72.05 | 5.45 | 6.69 | 72.71 | 5.53 |
| 9 | 473 | 6.03 | 72.40 | 5.43 | 6.07 | 72.07 | 5.49 | 6.00 | 72.31 | 5.48 |
| 10 | 497 | 6.03 | 72.40 | 5.43 | 6.01 | 72.04 | 5.47 | 6.00 | 71.80 | 5.44 |
| 11 | 466 | 6.03 | 72.40 | 5.43 | 6.03 | 72.15 | 5.43 | 5.99 | 72.40 | 5.37 |
| 12 | 463 | 5.11 | 74.43 | 6.80 | 5.10 | 74.23 | 6.72 | 5.00 | 74.12 | 6.54 |
| 13 | 471 | 4.76 | 77.54 | 4.97 | 4.72 | 76.98 | 5.03 | 4.68 | 77.58 | 5.06 |
| 14 | 484 | 4.21 | 79.50 | 5.00 | 4.15 | 78.96 | 5.09 | 4.26 | 79.42 | 5.10 |
| 15 | 488 | 5.85 | 72.79 | 5.69 | 5.81 | 72.24 | 5.68 | 5.88 | 72.61 | 5.61 |
| 16 | 468 | 5.69 | 73.16 | 5.93 | 5.49 | 71.73 | 6.23 | 5.72 | 72.64 | 5.90 |
| 17 | 478 | 5.76 | 74.07 | 4.77 | 5.82 | 74.06 | 4.93 | 5.74 | 73.73 | 4.86 |
| 18 | 480 | 5.76 | 74.07 | 4.77 | 5.75 | 74.06 | 4.90 | 5.77 | 74.19 | 4.88 |
| 19 | 450 | 5.18 | 75.54 | 5.41 | 5.10 | 74.76 | 5.51 | 5.21 | 75.45 | 5.38 |
| 20 | 449 | 5.18 | 75.54 | 5.41 | 5.20 | 74.97 | 5.33 | 5.18 | 75.23 | 5.34 |
| 21 | 470 | 5.18 | 75.54 | 5.41 | 4.84 | 70.95 | 5.20 | 5.26 | 75.30 | 5.32 |
| 22 | 454 | 5.69 | 73.16 | 5.93 | 5.53 | 71.70 | 5.89 | 5.64 | 73.12 | 5.96 |
| 23 | 445 | 4.86 | 75.02 | 7.11 | 4.56 | 70.49 | 6.81 | 4.80 | 74.58 | 7.04 |

ORGANIC EL DEVICE USE OF COMPOUNDS

EXAMPLES 1-23

Blue Emitting Organic EL Devices

A series of organic EL devices satisfying the requirements of the invention were constructed in the following manner:

(a) An indium tin oxide (ITO) coated glass substrate was ultrasonically cleaned in a commercial detergent, rinsed in deionized water, degreased in toluene vapor, and exposed to a strong oxidizing agent.

(b) A hole injecting layer of copper phthalocyanine (CuPc) having a thickness of 375 Å was deposited over the ITO on the substrate by vacuum evaporation from a tantalum boat.

(c) Onto the CuPc layer was deposited a 375 Å hole transporting layer of 4,4'-bis[N-(1-naphthyl)-N-phenylamino]biphenyl, also vacuum evaporated from a tantalum boat.

(d) A blue emitting electron transporting layer (300 Å) was deposited onto the hole transporting layer. This compound was also vacuum evaporated from a tantalum boat.

(e) Over the electron transporting layer was deposited a 300 Å electron injecting layer of aluminum trisoxine, again by vacuum evaporation from a tantalum boat.

(f) A 2000 Å cathode of a 10:1 atomic ratio of Mg to Ag was formed by vacuum deposition onto the aluminum trisoxine layer to complete the organic EL device.

In operation, the peak intensity wavelength of emission and the chromicity of emission in terms of the FIG. 1 C.I.E. x and y coordinates were recorded. This information is summarized below in Table III.

TABLE III

| Compound | Emission Maximum (nm) | C.I.E. X | Coord. Y |
|---|---|---|---|
| PC-1 | 495 | 0.193 | 0.308 |
| PC-2 | 483 | 0.187 | 0.287 |
| PC-3 | 483 | 0.180 | 0.269 |
| PC-4 | 483 | 0.187 | 0.290 |

TABLE III-continued

| Compound | Emission Maximum (nm) | C.I.E. X | Coord. Y |
|---|---|---|---|
| PC-5 | 483 | 0.180 | 0.264 |
| PC-6 | 475 | not meas. | not meas. |
| PC-7 | 478-491 | 0.197 | 0.322 |
| PC-8 | 484 | 0.180 | 0.272 |
| PC-9 | 476 | 0.174 | 0.242 |
| PC-10 | 497* | not meas. | not meas. |
| PC-11 | 481 | 0.178 | 0.259 |
| PC-12 | 480 | 0.185 | 0.270 |
| PC-13 | 471* | not meas. | not meas. |
| PC-14 | 484* | not meas. | not meas. |
| PC-15 | 487 | not meas. | not meas. |
| PC-16 | 468* | not meas. | not meas. |
| PC-17 | 507 | 0.210 | 0.347 |
| PC-18 | 491 | 0.197 | 0.342 |
| PC-19 | 450* | not meas. | not meas. |
| PC-20 | 449* | not meas. | not meas. |
| PC-21 | 470* | not meas. | not meas. |
| PC-22 | 454* | 0.160 | 0.175 |
| PC-23 | 445 | 0.156 | 0.136 |

*luminescence of powdered material used to form electron transporting layer

The luminescence of all of the aluminum chelates containing a phenolato ligand were measured as a powder and found to be blue emitting. When the aluminum chelates were incorporated in an organic EL device, the device was also blue emitting, although the emission peak was shifted to some extent to longer wavelengths as compared to the powder. The organic EL device with a C.I.E. chromaticity index nearest the green portion of the spectrum was that containing the aluminum chelate PC-17, shown in FIG. 1. The organic EL device with a C.I.E. chromaticity index at the shortest wavelength position was that containing the aluminum chelate PC-23, shown in FIG. 2. PC-17 in FIG. 1 lies within the blue-green portion of the spectrum defined by points D-C-480-499.2. E-23 in FIG. 1 lies within the pure blue portion of the spectrum defined by points C-B-460-480. All of the remaining aluminum chelates containing a phenolato ligand were located within these same blue emitting regions of the spectrum at points intermediate the E-17 and E-23 extremes.

The operation of the organic EL devices in terms of efficiency (measured in watts of emission per ampere of current), initial light output (initial intensity in milliwatts per cm$^2$) and stability (measured as the number of hours required for initial light output to decline to one half its original intensity when driven at a constant current of 20 mA/cm$^2$) is summarized in Table IV.

TABLE IV

| Compound | Efficiency (W/A) | ILO (mW/cm$^2$) | ½ ILO (hrs) |
|---|---|---|---|
| PC-1 | 0.023 | 0.46 | 180 |
| PC-2 | 0.022 | 0.44 | 186 |
| PC-3 | 0.023 | 0.46 | 260 |
| PC-4 | 0.022 | 0.44 | 156 |
| PC-5 | 0.025 | 0.50 | 503 |
| PC-6 | 0.024 | 0.48 | 400 |
| PC-7 | 0.021 | 0.42 | 607 |
| PC-8 | 0.029 | 0.58 | 132 |
| PC-9 | 0.030 | 0.60 | 120 |
| PC-10 | 0.020 | 0.40 | 200 |
| PC-11 | 0.022 | 0.44 | 177 |
| PC-12 | 0.030 | 0.60 | 52 |
| PC-13 | 0.024 | 0.48 | 461 |
| PC-14 | 0.022 | 0.44 | 109 |
| PC-15 | 0.019 | 0.38 | 263 |
| PC-16 | 0.020 | 0.40 | Not meas. |
| PC-17 | 0.014 | 0.28 | 407 |
| PC-18 | 0.023 | 0.47 | 329 |
| PC-19 | 0.031 | 0.62 | 200 |
| PC-20 | 0.028 | 0.56 | 156 |
| PC-21 | 0.033 | 0.66 | 156 |
| PC-22 | 0.045 | 0.90 | 60 |
| PC-23 | 0.033 | 0.66 | 84 |

Each of the organic EL devices were considered acceptable in terms of both initial efficiency and light output. Being able to maintain at least half of initial light output after 50 hours was taken as a measure of minimum acceptable stability. From Table II certain performance characteristics were correlated with the phenolato ligand of the aluminum chelate. Ligands derived from unsubstituted and methyl substituted hydroxybenzene ligands (PC-1-4) demonstrated acceptable chromaticitiy, maximum emission wavelengths, efficiencies and initial light output while exceeding minimum stability requirements. The methyl substituent produced a significant hypsochromic shift in emission as compared to the unsubstituted hydroxybenzene ligand. The ring position of the methyl substituent had little influence on any of the performance characteristics. When methyl substituents were replaced with phenyl substituents, very high levels of stability were realized while maintaining essentially similar initial performance characteristics (PC-5,6,7,13). The 2-naphthol ligand (PC-18) produced performance characteristics similar to those of the phenyl substituted hydroxyphenyl ligands, while the 1-naphthol ligand showed reduced efficiency and initial light output, but increased stability.

Taking both performance and chromaticity into account it can be seen that best overall performance was achieved with methyl or phenyl substituted hydroxybenzene phenolato ligands. Methyl substituents are considered representative of lower alkyl (1, 2 or 3 carbons atom) substituents while the phenyl substituents are considered representative of phenyl, biphenyl and naphthyl substituent group performance.

COMPARATIVE

Examples 24-29

Green Emitting Organic EL Devices

Organic EL devices were constructed similarly as in Examples 1-23, except that the phenolato ligand containing aluminum chelate was replaced by one of the following aluminum chelates:
C-24 Tris(8-quinolinolato)aluminum(III)
C-25 Tris(4-methyl-8-quinolinolato)aluminum(III)
C-26 Tris(5-methyl-8-quinolinolato)aluminum(III)
C-27 Tris(3,4-dimethyl-8-quinolinolato)aluinum(III)
C-28 Tris(4,6-dimethyl-8-quinolinolato)aluinum(III)
C-29 Tris(4,5-dimethyl-8-quinolinolato)aluminum(III)

The organic EL device containing C-24 exhibited an efficiency of 0.024 W/A and an initial light out of 0.48 mW/cm$^2$, indicating a performance characteristic similar to those of the Examples 1-23; however, the stability of C-24 was markedly superior to the compounds in Examples 1-23.

None of the control compounds were suitable for replacing any one of PC-1 through P-23, since in all instances the organic EL devices containnig C-24 to C-29 were clearly green emitting. This result is shown below in Table V.

TABLE V

| Compound | Emission Maximum (nm) | C.I.E. X | Coord. Y |
|---|---|---|---|
| C-24 | 533-536 | 0.315 | 0.550 |
| C-25 | 517 | 0.251 | 0.477 |
| C-26 | 560 | 0.412 | 0.560 |
| C-27 | 519 | not meas. | not meas. |
| C-28 | 536 | not meas. | not meas. |
| C-29 | 551 | not meas. | not meas. |

The most favorable chromaticity position measured was that of C-25. This point is shown in FIG. 1. It lies in the green portion of the spectrum.

COMPARATIVE EXAMPLES 30-32

Chelates with STrongly Electron Withdrawing Ring Substituents

The following compounds were prepared with the intention that they be substituted for one of aluminum chelate compounds PC-1 to P-23 in Example 1:
C-30 Bis(2-methyl--8-quinolinolato)(4-chlorophenolato)aluminum(III)
C-31 Bis(2-methyl--8-quinolinolato)(4-cyanophenolato)aluminum(III)
C-32 Bis(2-methyl--8-quinolinolato)(4-trifluormethyl-phenolato)aluminum(III)

Comparisons of elemental analyses of initial materials and vacuum vapor deposited materials revealed that a significant degree of decomposition had occurred in coverting these compounds to the vapor phase and back to a solid.

Organic EL devices were constructed similarly as in Examples 1-23, except that the phenolato ligand containing aluminum chelate was replaced using C-30 or C-31 as a starting material for vacuum vapor deposition. The organic EL device constructed starting with C-30 exhibited a peak wavelength of emission of 493 nm and an efficiency of 0.022 W/A. The organic EL device constructed starting with C-31 exhibited a peak wavelength of emission of 530 nm and an efficiency of 0.018 W/A. Taking both peak emission wavelength and efficiency into account, C-30 and C-31 produced inferior blue emitting organic EL devices as compared with PC-1 to PC-23.

COMPARATIVE EXAMPLES 33-34

Chelates with STrongly Electron Donating Ring Substituents

Organic EL devices were constructed similarly as in Examples 1-23, except that the phenolato ligand containing aluminum chelate was replaced by one of the following aluminum chelates:

C-33  Bis(2-methyl-8-quinolinolato)(4-methoxyphenolato)aluminum(III)

C-34  Bis(2-methyl-8-quinolinolato)(3,5-dimethoxyphenolato)aluminum(III)

The organic EL device constructed starting with C-33 exhibited a peak wavelength of emission of 490 nm and an efficiency of 0.008 W/A—i.e., luminescence was objectionably weak. The organic EL device constructed starting with C-34 exhibited a peak wavelength of emission of 491 nm. Efficiency was 0.028 W/A with an initial light output of 0.56 mW/cm$^2$, but the device declined to ½ its initial light output in only hours, indicating inadequate stability.

COMPARATIVE EXAMPLE 35

Chelate with Phenolato Ligand With Fused Noncarbocyclic Ring

The purpose of this comparison is to demonstrate the importance of the ring fused with the hydroxybenzene ring in the phenolato ligand being a carbocyclic ring.

An organic EL device was constructed similarly as in Examples 1-23, except that the phenolato ligand containing aluminum chelate was replaced by the following aluminum chelate:

C-35  Bis(2-methyl-8-quinolinolato)(5-quinolinolato)aluminum(III)

The organic EL device exhibited a relatively long maximum emission wavelength of 500 and was judged unacceptable in performance based on a decline to ½ initial light output in less than one hour.

EXAMPLES 36-39

Doping to Attain Shorter Wavelengths of Emission

A series of organic EL devices were constructed identically as in Example 7, except that PC-7 was doped with varied amounts of perylene (FD-1), ranging from 0.5 to 3 mole percent, based on PC-7. The results are summarized below in Tables VI and VII.

TABLE VI

| Example | Mole % Dopant | FIG. 1 C.I.E. X | Coord. Y |
|---|---|---|---|
| 7 | 0 | 0.20 | 0.32 |
| 36 | 0.50 | 0.16 | 0.19 |
| 37 | 1.00 | 0.17 | 0.21 |
| 38 | 2.00 | 0.17 | 0.18 |
| 39 | 3.00 | 0.19 | 0.29 |

From Table VI it is apparent that all concentrations of FD-1, ranging from 0.5 to 3 mole per percent, based on PC-7, were effective to shift the emission hues of the organic EL devices of Examples 36 to 39 to shorter wavelengths. The points E-7 (x-0.20, y=0.30) and E-36 (x=0.16, y=0.21) in FIG. 1 demonstrate the hue shift that can be provided by FD-1. The data indicate that a concentration range of from 0.2 to 3 mole percent is a preferred range, with from 0.5 to 2 mole percent being an optimum range.

TABLE VII

| Example | EL Eff. (w/A) | Volts @ 20 mA/cm$^2$ | ILO mW/cm$^2$ | ½ ILO hrs. |
|---|---|---|---|---|
| 7 | 0.021 | 8.3 | 0.42 | 607 |
| 36 | 0.025 | 8.0 | 0.50 | 1215 |
| 37 | 0.019 | 8.5 | 0.38 | 1860 |
| 38 | 0.018 | 8.2 | 0.36 | 1750 |
| 39 | 0.018 | 8.2 | 0.36 | 1715 |

Turning to Table VII, it is apparent that the overall efficiency of the organic EL devices first increased and then declined somewhat as the level of dopant increased, but this was more than offset by very dramatic increases in stability being realized.

EXAMPLES 40-45

Doping Varied Phenolato Ligand Aluminum Chelates

A series of organic EL devices were constructed similarly as in Examples 1-23, except that FD-1 was either included in the electron transporting layer in a concentration of 1 mole percent, based on the phenolato ligand aluminum chelate host, or omitted. The results are summarized below in Tables VIII and IX.

TABLE VIII

| Example | Host/Dopant | FIG. 1 C.I.E. X | Coord. Y |
|---|---|---|---|
| 40 | PC-5/FD-1 | 0.16 | 0.19 |
| 41 | PC-5 | 0.18 | 0.26 |
| 42 | PC-13/FD-1 | 0.15 | 0.16 |
| 43 | PC-13 | 0.17 | 0.23 |
| 44 | PC-18/FD-1 | 0.17 | 0.23 |
| 45 | PC-18 | 0.19 | 0.31 |

From Table VIII it is apparent that a hypsochromic shift in the hue of emission was achieved with each of the varied phenolato ligand aluminum chelate hosts.

TABLE IX

| Example | EL Eff. (w/A) | Volts @ 20 mA/cm$^2$ | ILO mW/cm$^2$ | ½ ILO hrs. |
|---|---|---|---|---|
| 40 | 0.020 | 9.0 | 0.40 | >1200 |
| 41 | 0.025 | 8.9 | 0.48 | 655 |
| 42 | 0.019 | 8.0 | 0.38 | 972 |
| 43 | 0.024 | 8.0 | 0.48 | 462 |
| 44 | 0.021 | 8.1 | 0.42 | 1165 |
| 45 | 0.019 | 7.8 | 0.38 | 180 |

Turning to Table IX, it apparent that the dopant in every instance produced a marked increase in the stability of the organic EL devices.

The invention has been described in detail with particular reference to preferred embodiments thereof, but it will be understood that variations and modifications can be effected within the spirit and scope of the invention.

What is claimed is:

1. A blue emitting luminescent composition comprised of an aluminum chelate of the formula:

(R$^S$—Q)$_2$—Al—O—L where

Q in each occurrence represents a substituted 8-quinolinolato ligand,

R$^S$ represents an 8-quinolinolato ring substituent chosen to block sterically the attachment of more than two substituted 8-quinolinolato ligands to the aluminum atom, and L is a phenyl or aromatic fused-ring moiety which can be substituted with hydrocarbon groups such that L has from 6 to 24 carbon atoms.

2. A blue emitting luminescent composition according to claim 1 further characterized in that $R^S$ is a 2-position substituent of the 8-quinolinolato ring 3. A blue emitting luminescent composition according to claim 2 further characterized in that $R^S$ is an electron donating substituent.

4. A blue emitting luminescent composition according to claim 3 further characterized in that $R^S$ is chosen from the group consisting of amino, oxy and hydrocarbon groups containing up to 10 carbon atoms.

5. A blue emitting luminescent composition according to claim 4 further characterized in that $R^S$ is a hydrocarbon containing from 1 to 6 carbon atoms.

6. A blue emitting luminescent composition according to claim 1 further characterized in that the 8-quinololato ring nucleus includes a 4-position ring substituent that is electron donating.

7. A blue emitting luminescent composition according to claim 6 further characterized in that the 4-position ring substituent is chosen from among amino, oxy and hydrocarbon groups containing up to 10 carbon atoms.

8. A blue emitting luminescent composition according to claim 1 further characterized in that the 8-quinolinolato ring nucleus includes in at least one of its 5, 6 and 7 ring positions a substituent that is electron accepting.

9. A blue emitting luminescent composition according to claim 8 further characterized in that each of the 5, 6 and 7 ring position electron accepting substituents is chosen from among electron accepting cyano, halogen, and α-haloalkyl, α-haloalkoxy, amido, sulfonyl, carbonyl, carbonyloxy and oxycarbonyl substituents containing up to 10 carbon atoms.

10. A blue emitting luminescent composition according to claim 1 further characterized in that the aluminum chelate satisfies the formula:

where $R^2$ represents an electron donating substituent, $R^3$ and $R^4$ each independently represent hydrogen or an electron donating substituent, $R^5$, $R^6$ and $R^7$ each independently represent hydrogen or an electron accepting substituent, and L is a phenyl or aromatic fused-ring moiety which can be substituted with hydrocarbon groups such that L has from 7 to 18 carbon atoms.

11. A blue emitting luminescent composition according to claim 10 further characterized in that the electron donating substituents are independently chosen from the group consisting of —R′, —OR′ and —N(R″)R′, where R′ is a hydrocarbon containing up to 6 carbon atoms and R″ is hydrogen or R′ and the electron accepting substituents are each independently chosen from among electron accepting cyano, halogen, and α-haloalkyl, α-haloalkoxy, amido, sulfonyl, carbonyl, carbonyloxy and oxycarbonyl substituents containing up to 6 carbon atoms.

12. A blue emitting luminescent composition according to claim 1 further characterized in that the hydrocarbon includes at least one aliphatic substituent of the phenyl moiety.

13. A blue emitting luminescent composition according to claim 12 further characterized in that the aliphatic substituent contains from 1 to 10 carbon atoms.

14. A blue emitting luminescent composition according to claim 13 further characterized in that the hydrocarbon includes at least one alkyl substituent of the phenyl moiety.

15. A blue emitting luminescent composition according to claim 13 further characterized in that the hydrocarbon includes at least two alkyl substituents of the phenyl moiety.

16. A blue emitting luminescent composition according to claim 14 further characterized in that the aliphatic substituent contains from 1 to 3 carbon atoms.

17. A blue emitting luminescent composition An internal junction organic electroluminescent device according to claim 1 further characterized in that a benzo ring is fused with the phenyl moiety.

18. A blue emitting luminescent composition according to claim 1 further characterized in that the hydrocarbon includes at least one aromatic substituent of the phenyl moiety.

19. A blue emitting luminescent composition according to claim 18 further characterized in that the aromatic substituent is comprised of a phenyl ring.

20. A blue emitting luminescent composition according to claim 1 further characterized in that the aluminum chelate satisfies the formula:

where

Q in each occurrence represents a substituted 8-quinolinolato ring nucleus, $R^2$ in each occurrence represents a 2-position electron donating substituent of the 8-quinolinolato ring nucleus, and $L^1$, $L^2$, $L^3$, $L^4$ and $L^5$ collectively contain 12 or fewer carbon atoms and each independently represent hydrogen or hydrocarbon groups of from 1 to 12 carbon atoms, with the proviso that $L^1$ and $L^2$ together or $L^2$ and $L^3$ together can form a fused benzo ring.

21. A blue emitting luminescent composition according to claim 1 further characterized in that the luminescent layer additionally includes a fluorescent 22. A blue emitting luminescent composition according to claim 21 further characterized in that the fluorescent dye is chosen to provide a favored recombination site for holes and electrons and is blue emitting.

23. A blue emitting luminescent composition according to claim 22 further characterized in that the blue emitting fluorescent dye exhibits a shorter wavelength emission peak than the aluminum chelate.

24. A blue emitting luminescent composition according to claim 22 further characterized in that the blue emitting fluorescent dye contains a stabilizing aromatic chromophoric unit containing at least 5 fused carbocyclic aromatic rings.

25. A blue emitting luminescent composition according to claim 24 further characterized in that the chromophoric unit contains from 20 to 40 ring carbon atoms.

26. A blue emitting luminescent composition according to claim 25 further characterized in that the fluorescent dye chromophoric unit is chosen from among those containing a perylene, benzopyrene, benzochrysene, benzonaphthacene, picene, pentaphene, pentacene, hexacene or anthanthrene nucleus.

27. A blue emitting luminescent composition according to claim 24 further characterized in that the fluorescent dye is present in a concentration ranging from 0.05 to 5 mole percent.

28. A blue emitting luminescent composition according to claim 27 further characterized in that the fluorescent dye is present in a concentration ranging from 0.2 to 3 mole percent.

29. A blue emitting luminescent composition according to claim 27 further characterized in that the fluorescent dye is present in a concentration ranging from 0.5 to 2 mole percent.

30. A blue emitting luminescent composition comprised of an aluminum chelate chosen from the group consisting of bis(2-methyl-8-quinolinato)(phenolato)-aluminum(III);
bis(2-methyl-8-quinolinato)(ortho-cresolato)-aluminumn(III);
bis(2-methyl-8-quinolinato)(meta-cresolato)-aluminum(III);
bis(2-methyl-8-quinolinato)(para-cresolato)-aluminum(III);
bis(2-methyl-8-quinolinato)(ortho-phenylphenolato)-aluminum(III);
bis(2-methyl-8-quinolinato)(meta-phenylphenolato)aluminum(III);
bis(2-methyl-8-quinolinato)(para-phenylphenolato)-aluminum(III);
bis(2-methyl-8-quinolinato)(2,3-dimethylphenolato)aluminum(III);
bis(2-methyl-8-quinolinato)(2,6-dimethylphenolato)aluminum(III);
bis(2-methyl-8-quinolinato)(3,4-dimethylphenolato)aluminum(III);
bis(2-methyl-8-quinolinato)(3,5-dimethylphenolato)aluminum(III);
bis(2-methyl-8-quinolinato)(3,5-di-tert.-butylphenolato)aluminum(III);
bis(2-methyl-8-quinolinato)(2,6-diphenylphenolato)aluminum(III);
bis(2-methyl-8-quinolinato)(2,4,6-tri-phenylphenolato)aluminum(III);
bis(2-methyl-8-quinolinato)(2,3,6-tri-methylphenolato)aluminum(III);
bis(2-methyl-8-quinolinato)(2,3,5,6-tetramethylphenolato)aluminum(III);
bis(2-methyl-8-quinolinato)(1-naphtholato)aluminum(III);
bis(2-methyl-8-quinolinato)(2-naphtholato)aluminum(III);
bis(2,4-dimethyl-8-quinolinato)(ortho-phenylphenolato)aluminum(III);
bis(2,4-dimethyl-8-quinolinato)(para-phenylphenolato)aluminum(III);
bis(2,4-dimethyl-8-quinolinato)(meta-phenylphenolato)aluminum(III);
bis(2,4-dimethyl-8-quinolinato)(3,5-dimethylphenolato)aluminum(III); and
bis(2,4-dimethyl-8-quinolinato)(3,5-di-tert-butylphenolato)aluminum(III).

* * * * *